(12) United States Patent
Bittar et al.

(10) Patent No.: US 9,596,878 B2
(45) Date of Patent: Mar. 21, 2017

(54) USE OF CANTHAXANTHIN

(71) Applicant: DSM IP ASSETS B.V., Heerlen (NL)

(72) Inventors: Isaac Bittar, Basel (CH); Rafael Gustavo Hermes, Basel (CH); Catherine Hamelin, Basel (CH); Fernando Cisneros, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/898,988

(22) PCT Filed: Jun. 10, 2014

(86) PCT No.: PCT/EP2014/062028
§ 371 (c)(1),
(2) Date: Dec. 16, 2015

(87) PCT Pub. No.: WO2014/202433
PCT Pub. Date: Dec. 24, 2014

(65) Prior Publication Data
US 2016/0128359 A1 May 12, 2016

(30) Foreign Application Priority Data
Jun. 18, 2013 (EP) .................................. 13172380

(51) Int. Cl.
*A01N 45/00* (2006.01)
*A23L 1/32* (2006.01)
*A23K 1/16* (2006.01)
*A23K 1/18* (2006.01)
*A61K 31/122* (2006.01)
*A61K 31/593* (2006.01)

(52) U.S. Cl.
CPC .......... *A23L 1/3212* (2013.01); *A23K 1/1603* (2013.01); *A23K 1/1606* (2013.01); *A23K 1/1826* (2013.01); *A23K 20/174* (2016.05); *A23K 20/179* (2016.05); *A23K 50/75* (2016.05); *A23L 15/00* (2016.08); *A23L 15/30* (2016.08); *A23L 33/155* (2016.08); *A61K 31/122* (2013.01); *A61K 31/593* (2013.01); *A23V 2002/00* (2013.01)

(58) Field of Classification Search
CPC .. A23K 1/1606; A23K 1/1603; A23K 1/1826; A23K 1/303; A23K 1/3212; A23K 20/174; A23K 20/179; A23K 50/75; A61K 31/122; A61K 31/593; A23L 1/3212; A23L 1/1603; A23L 1/1606; A23L 1/1826; A23L 33/155; A23L 15/00; A23L 15/30; A23V 2002/00
USPC .......................................................... 514/167
See application file for complete search history.

(56) References Cited

U.S. PATENT DOCUMENTS

| | | | |
|---|---|---|---|
| 5,043,170 A | 8/1991 | Borenstein et al. | |
| 2010/0186674 A1* | 7/2010 | Cahill, Jr. ............ | A01K 45/007 119/6.8 |

FOREIGN PATENT DOCUMENTS

| | | |
|---|---|---|
| EP | 0 033 197 | 8/1981 |
| WO | 2011/015651 | 2/2011 |
| WO | WO 2011/015651 | 2/2011 |

OTHER PUBLICATIONS

International Search Report for PCT/EP2014/062028, mailed Aug. 26, 2014, 3 pages.

* cited by examiner

*Primary Examiner* — T. Victor Oh
(74) *Attorney, Agent, or Firm* — Nixon & Vanderhye P.C.

(57) ABSTRACT

The present invention relates to the use of canthaxanthin and at least one vitamin D metabolite, preferably 25-hydroxy vitamin D3 (25-OH D3), for improving internal egg quality. Interior egg quality, usually expressed in Haugh Units, is prolonged by feeding the laying poultry a diet containing canthaxanthin and 25-hydroxy vitamin D3.

6 Claims, No Drawings

USE OF CANTHAXANTHIN

This application is the U.S. national phase of International Application No. PCT/EP2014/062028 filed 10 Jun. 2014, which designated the U.S. and claims priority to EP Patent Application No. 13172380.1 filed 18 Jun. 2013, the entire contents of each of which are hereby incorporated by reference.

FIELD OF THE INVENTION

The present invention is in the general field of poultry farming and relates particularly to the feeding of laying fowl or layers.

The present invention relates to the use of canthaxanthin optionally in combination with at least one vitamin D metabolite, preferably 25-hydroxy vitamin D3 (25-OH D3) as feed additive, for improving egg quality of poultry layers.

In a particular aspect, it relates to a method of feeding female birds with a feed formulation which enhances, for example, interior egg quality, as well as egg production, and/or egg shell quality. This invention also relates to the eggs with improved egg shells obtained from birds fed a diet of this invention. Poultry diets of this invention are typically diets which include canthaxanthin optionally in combination with at least one vitamin D metabolite in an amount such that degradation of the interior quality of eggs is retarded.

More particularly the invention relates to the use of canthaxanthin, optionally in combination with 25-hydroxy vitamin D3 in the manufacture of a feed composition for increasing Haugh unit value and/or for strengthening vitelline membrane of poultry eggs.

This invention also relates to improved poultry farming. Thus, it relates to methods which provide improved egg production. These methods comprise obtaining an increase in yield of marketable eggs from laying hens. The increase is provided by feeding hens a diet of this invention.

BACKGROUND OF THE INVENTION

It is well known, that the internal quality of eggs is diminished with time. The loss in quality attributes of the albumen and yoke is a function of temperature and movement of carbon dioxide through the shell. Low temperatures decrease the rate of loss in Haugh units—a standard measure of interior egg quality—and thus it is recommended that eggs be stored at temperatures close to the freezing point, a procedure which, as a practical matter, is not always feasible. To reduce rate of carbon dioxide (and moisture) loss various shell treatments have been utilized, such as spraying oil on the eggs.

Freshness is one of the most important parameters in indicating the internal quality of an egg. The moment an egg is laid, it is starting to become stale. When the housekeeper cracks an egg, he/she is expecting to find a series of visual clues indicating how fresh the egg is. The watery status of the white and the consistency of the vitelline membrane (yolk membrane) are two parameters to indicate the freshness of an egg. This is also important for the egg and the bakery industry, because a stale egg will fail to rise properly when battered.

When an egg is broken onto a flat surface has a watery, spread-out white, this usually indicates that the egg is stale. The height of the albumin then is very important for the freshness of the egg, and it is measured as Haugh unit value. The highest the value, the fresher the egg is. It is known, when egg ages, the Haugh units value decrease and therefore the egg freshness is reduced. Haugh units comes from the height of the albumin adjusted by the size of the egg.

Therefore, any method or feeding practice that can increase or preserve the Haugh unit value, is considered highly beneficial for the egg industry.

A way has been discovered for reducing, if not eliminating, the need for refrigeration and spray oiling on eggs as a means of preserving interior egg quality.

To ameliorate the problem of interior egg degradation with time, the following procedures have been recommended heretofore:
1. Gather eggs three to four times per day.
2. Clean the eggs promptly after gathering and cool for 12-24 hours at 13° C. or preferably 10° C. before packing in cases or cartons.
3. Keep the eggs at between 60 to 85%, preferably 70 to 80%, relative humidity.
4. Resort to careful handling.
5. Use proper packing using precooled containers only.
6. Resort to frequent marketing of not less than twice a week.
7. Use speedy, refrigerated transportation and make frequent deliveries to sales outlets, preferably at least five times per week.
8. Use adequately refrigerated holding spaces at sales outlets.
9. Keep the eggs in home refrigerators at 7° C. to 13° C., and preferably use all of the eggs within one week.

The demand for poultry eggs, especially chicken eggs expanded considerably over the last decade. The poultry industry has grown from a home industry to a large scale manufacturing industry in which tens of thousands of eggs are produced daily at single farms or egg laying installations. Some eggs are produced for eating and some eggs are produced for hatching. One problem with such large scale egg producing is premature reduction in interior egg quality as a function of time. That is, unless eggs are handled and/or treated in accordance with the above 9-point program, their quality as regards internal qualities of the albumen and yolk may deteriorate faster than would be desired. Moreover, a way of simplifying egg production, distribution, marketing, etc. with concomitant reduction in refrigeration requirements would be a welcome contribution to the art.

Another problem associated with large scale egg production is breakage. Even a slight crack in an egg makes it unsuitable for hatching and most other marketing purposes. It is estimated that some six percent of all eggs produced are lost for marketing because of cracking or breakage. Shell strength is very important to inhibit breakage. The stronger the egg shell, the less likely the egg will be cracked or broken. Machinery and techniques necessary for carefully handling the eggs to avoid breakage are expensive and time consuming.

Another substantial loss of egg production, estimated to be about a seven percent loss, is the production of shell-less eggs. Any reduction in shell-less eggs can be an important factor in large scale egg production.

Another important measurement is the strength of the vitelline membrane. Very often the bakery, pasta and in general the egg products industry has to separate the egg from the white, in order to prepare different dishes and formulas. This is one of the most important quality criteria for the industrial egg sector. Therefore, when possible a strong and resistant egg yolk will be always preferable.

SUMMARY OF THE INVENTION

In accordance with the present invention it has been surprisingly found that the egg quality, in particular the freshness of poultry eggs can be improved and/or prolonged by administering to the animals an effective amount of canthaxanthin and optionally 25-OH-D3.

Inventors have discovered that internal egg quality can be maintained at a higher level by feeding laying poultry a diet containing canthaxanthin and optionally 25-OH-D3. In other words, this invention provides, in one of its embodiments, a process for reducing the rate of internal egg quality degradation which comprises feeding a laying poultry hen a diet which contains canthaxanthin and optionally 25-OH-D3 such that the rate in decrease in Haugh unit value of the eggs from said hen is reduced as compared to the rate of such decrease under the same conditions with the same diet absent canthaxanthin and optionally 25-OH-D3. In this process, the amount of canthaxanthin and optionally 25-OH-D3 is usually within the range of about 0.25 to about 3.5 weight percent, preferably between about 0.75 to about 1.5 weight percent.

Accordingly, we have discovered that egg production, egg quality, notably internal egg quality, and/or egg shell quality of poultry eggs is enhanced if, besides adding canthaxanthin and optionally 25-OH-D3 to the diet. The improvement can result in the production of more collectable eggs, which with broiler breeder hens means more eggs that are settable in incubators.

DETAILED DESCRIPTION OF THE INVENTION

As used throughout the specification and claims, the following definitions apply:

"Vitamin D metabolite" means any metabolite of Vitamin D as for example 25-hydroxy vitamin D3, 1,25-dihydroxy vitamin D3 or 24,25-dihydroxy vitamin D3.

"25-OH D3" refers specifically to 25-hydroxy vitamin D3.

"Poultry" is meant to include turkeys, ducks and chickens (including but not limited to broiler chicks, layers, breeders).

Canthaxanthin and 25-OH D3 may be obtained from any source, and a composition thereof may be prepared using convenient technology.

The Haugh unit is a mathematical relationship between the egg weight and albumen. The test was introduced by Raymond Haugh and is an important industry measure of egg quality next to other measures such as shell thickness and strength.

An egg is weighed, then broken onto a flat surface (breakout method), and a micrometer used to determine the height of the thick albumen (egg white) that immediately surrounds the yolk. The height, correlated with the weight, determines the Haugh unit, or HU, rating. The higher the number, the better the quality of the egg (fresher, higher quality eggs have thicker whites). Although the measurement determines the protein content and freshness of the egg, it does not measure other important nutrient contents such as the micronutrient or vitamins present in the egg.

The formula for calculating the Haugh unit is:

$$HU=100*\log(h-1.7w^{0.37}+7.6)$$

Where:
HU=Haugh unit
h=observed height of the albumen in millimeters
w=weight of egg in grams In a first aspect, one or more feed compositions suitable for poultry use are provided to administer canthaxanthin and 25-OH D3 as nutrients to improve egg quality of poultry layers.

In a second aspect, a poultry feed is provided which comprises from about 10 μg/kg to about 100 μg/kg of 25-OH D3 and from about 2 to 100 ppm canthaxanthin, preferably 2 to 10 ppm.

In another aspect, a premix composition for poultry feed comprising 25-hydroxy vitamin D3 and canthaxanthin is provided.

Canthaxanthin and 25-hydroxy vitamin D3 are suitably administered together with the food. The term food as used herein comprises both solid and liquid food as well as drinking fluids such as drinking water. Particularly, inventive ingredients can be added as a formulated powder to a premix containing other minerals, vitamins, amino acids and trace elements which is added to regular animal food and thorough mixing to achieve even distribution therein.

In the manufacture of poultry feed in accordance with the invention, from about 2 ppm to 100 ppm, preferably 2-10 ppm of canthaxanthin and from about 10μ/kg to about 100 μg/kg of 25-hydroxy vitamin D3 are added to regular poultry food. Alternatively, a food premix may be prepared on the basis of regular food components by adding these active ingredients to such food components in higher concentration.

As noted above, this invention involves, inter alia, a method for reducing degradation of internal egg quality. In one of its forms, this method involves a process for obtaining an egg crop having a reduced rate of internal egg quality degradation which comprises (i) preparing a poultry diet which contains from about 0.25 to about 3.0 weight percent canthaxanthin and optionally 25-OH D3, (ii) feeding such diet to laying poultry, and (iii) recovering an egg crop therefrom in which the rate in decrease in Haugh unit value of the eggs is reduced as compared to the rate of such decrease under the same conditions with the same diet absent canthaxanthin and optionally 25-OH D3.

In another of its forms, the present invention relates to a method of improving the egg shell characteristics, e.g. egg shell strength of eggs from laying poultry. A convenient means of measuring egg shell strength is by measuring the specific gravity of the egg. This is simply done by immersing the egg in solutions of salt water of varying strengths. It is well known in the art that specific gravity correlates with egg shell strength. As specific gravity of the egg is raised, the strength of the egg shell is increased.

This latter method of this invention can also improve egg shell thickness, and/or decrease the number of eggs produced without shells.

According to the present invention the 25-OH-D3 compound is available under the Trademark ROVIMIX® Hy-D® 1.25% and canthaxanthin under the Trademark CAROPHYLL®Red. A combination product of both, canthaxanthin and 25-OH-D3 is available under the Trademark MAXICHICK®.

According to the present invention it is further advantageous if the composition also contains one or more of the following ingredients: Vitamin A, Vitamin E, Biotin, copper (e.g. as $CuSO_4$), zinc (e.g. as $ZnSO_4$), cobalt (e.g. as $CoSO_4$), selenium (e.g. as $Na_2SeO_3$), iodine (e.g. as KI), manganese (e.g. as $MnSO_4$) and/or calcium (e.g. as $CaSO_4$).

The following non-limiting Examples are presented to better illustrate the invention.

EXAMPLE

Effect of Carophyll Red (Canthaxanthin) and 25-OH D3 on Freshness of the Egg

Carophyll Red combined with HyD used in the feed of the laying hen, can increase the perception of freshness of the egg, thanks to its capacity to preserve the height of the albumin (Haugh unit value), and increase the strength of the vitelline membrane. These were unexpected results from trials designed to test the reproductive performance of the hen.

Haugh Unit:

In an experiment, laying hens were used to test the effect of the dietary inclusion of MaxiChick® (a combination of Carophyll® Red and HyD®) on their productive performance and shell quality. A total of Two hundred and forty Lohmann hens (60 weeks old) were distributed to three treatments with 10 reps c/u. Repetition was cage containing 8 chickens. The experimental diets contained soy and wheat, however the main source of grain changed from one treatment to the next. Being either corn (Control) or sorghum (Sor) or sorghum added with MaxiChick® (MC). Diets were isocaloric (2.75 Mcal ME), isonitrogenous (17.5% crude protein) and similar levels of Ca, P, vitamins and minerals. MaxiChick provided 6 mg and 69 mg canthaxanthin/kg of 25·OHD3 per kg of feed. The experiment lasted two cycles of 28 days each. During the experimental period feed intake, yolk pigmentation (DSMYCF), shell strength and Haugh units were measured. Data were subjected to analysis of variance and the means were compared by Tukey test ($P<0.05$).

Production performance data from the hens are shown in Table 1.

TABLE 1

Productive response of laying hens subjected to the ingestion of MC in diets based on corn or sorghum

|  | Maiz | Sorgo + MC | Sorgo | P |
|---|---|---|---|---|
| Laying, % | 70.14 | 72.17 | 71.15 | 0.2148 |
| Feed intake, g/d | 114 | 115 | 116 | 0.3351 |
| Yolk color (DSMYCF) | $8^{ab}$ | $12^a$ | $3^b$ | 0.0025 |
| Shell Resistance, kgf | $3.24^b$ | $4.12^a$ | $3.13^b$ | 0.0037 |
| Haugh Units | $85.15^b$ | $86.98^a$ | $84.41^b$ | 0.0781 | means (10 repetitions each) without common superscripts are different ($P < 0.05$).

Most of the variables have been studied in the past and the results were expected, being this a secondary study of a project aimed at knowing the effect of MaxiChick on the performance and quality of the progeny. The difference in Haugh units was not expected in this study however it fits with testimonial evidence coming from customers using MaxiChick. MaxiChick fed hens laid eggs capable to keep their freshness for longer (Higher Haugh unites value).

In a different trial, also looking at the effect of MaxiChick® on the performance of broiler breeders, another unexpected result was observed. The vitelline membrane strength was enhanced by the use of MaxiChick®. The resistance of the yolk is very important for the industry and therefore, everything that we can do to increase the yolk resistance is welcomed by the eggs producers.

The experiment was carried out with four groups (two flocks×two batches/flock) of 3800 breeders each. The four groups were placed in the laying house equipped with a floor system (⅓ slatt, ⅔ litter). Zootechnical criteria were recorded per batch between 21 and 60 weeks of age. Average egg size was evaluated once a month. Egg quality measurements, hatching test and individual day-old chick performance estimate were performed at 3 different ages: 32, 47 and 57 weeks of age of the hens.

On Table 2 the results are shown for the measurement at 47 weeks. The fact that the vitelline membrane was more rigid and more membrane rupture force was needed, are related to a stronger vitelline membrane, that as a consequence it will be more easily separated for the white for bakery, cooking and/or industrial purposes.

TABLE 2

Egg Quality Measurements according to treatment at 47 wks

| Variable | Control | MaxiChick ® | Average | Statistics |
|---|---|---|---|---|
| Number of eggs | 420 | 420 | 840 |  |
| Egg weight, g | 61.5 | 61.7 | 61.6 | P < 0.463 |
| Shell static stiffness (N/mm) | 0 | 131.8 | 132.4 | P < 0.434 |
| Shell fracture force (N) | 35.0 | 34.5 | 34.7 | P, 0.254 |
| Vitelline membrane rigidity (mN/mm) | 7.8 | 8.1 | 7.9 | P < 0.001 |
| Vitelline membrane rupture force (mN) | 43.3 | 44.7 | 44 | P < 0.014 |

In both studies, it has been shown that the combination of Canthaxanthin and HyD can increased the quality of the egg by the means of increased Haugh Units and the yolk resistance. Those two parameters are key to evaluate the internal quality of the egg.

The invention claimed is:

1. A method for improving egg quality as expressed in terms of Haugh units, which comprises administering to a layer hen in need of such treatment a diet comprising an amount of about 2 ppm to 100 ppm of canthaxanthin and about 10 μg/kg to about 100 μg/kg of 25-hydroxy vitamin D3 sufficient to significantly increase the rate of the Haugh unit value of the eggs from the hen as compared with a diet which is absent the canthaxantin and 25-hydroxy vitamin D3.

2. The method according to claim 1, wherein the diet comprises 2 to 10 ppm of the canthaxanthin.

3. A process for reducing the rate of internal egg quality degradation as expressed in terms of Haugh units which comprises feeding a laying poultry hen a diet which contains from about 2 ppm to 100 ppm of canthaxanthin and about 10 μg/kg to about 100 μg/kg of 25-hydroxy vitamin D3 sufficient such that the rate in decrease in Haugh unit value of the eggs from said hen is significantly reduced as compared to the rate of such decrease under the same conditions with the same diet absent the canthaxanthin and the 25-hydroxy vitamin D3.

4. The process according to claim 3, wherein the diet comprises 2 to 10 ppm of the canthaxanthin.

5. A process for obtaining an egg crop having a reduced rate of internal egg quality degradation expressed as Haugh units which comprises:
  (i) feeding laying poultry a diet which contains from about 2 ppm to 100 ppm of canthaxanthin and from about 10 μg/kg to about 100 μg/kg of 25-hydroxy vitamin D3; and
  (ii) recovering an egg crop from the laying poultry fed according to step (i) in which the rate in decrease in Haugh unit value of eggs in the egg crop is significantly reduced as compared to the rate of such decrease under the same conditions with the same diet absent canthaxanthin and 25-hydroxy vitamin D3.

6. The process according to claim 5, wherein the diet comprises 2 to 10 ppm of the canthaxanthin.

* * * * *